(12) United States Patent
Krishnan

(10) Patent No.: US 7,907,264 B1
(45) Date of Patent: Mar. 15, 2011

(54) MEASUREMENT OF THIN FILM POROSITY

(75) Inventor: Shankar Krishnan, Santa Clara, CA (US)

(73) Assignee: KLA-Tencor Corporation, Milpitas, CA (US)

(*) Notice: Subject to any disclaimer, the term of this patent is extended or adjusted under 35 U.S.C. 154(b) by 366 days.

(21) Appl. No.: 12/193,450

(22) Filed: Aug. 18, 2008

Related U.S. Application Data

(60) Provisional application No. 60/970,549, filed on Sep. 7, 2007.

(51) Int. Cl.
*G01N 21/41* (2006.01)
*G01N 15/08* (2006.01)
*G01B 11/00* (2006.01)
*G01B 11/22* (2006.01)
*G01R 31/26* (2006.01)

(52) U.S. Cl. ............ 356/128; 356/626; 356/627; 73/38; 438/16

(58) Field of Classification Search ................. None
See application file for complete search history.

(56) References Cited

U.S. PATENT DOCUMENTS

| | | | |
|---|---|---|---|
| 6,365,266 B1 * | 4/2002 | MacDougall et al. | 428/304.4 |
| 6,435,008 B2 * | 8/2002 | Baklanov et al. | 73/38 |
| 6,593,251 B2 * | 7/2003 | Baklanov et al. | 438/778 |
| 7,042,570 B2 * | 5/2006 | Sailor et al. | 356/445 |
| 7,209,234 B2 * | 4/2007 | Woollam et al. | 356/369 |
| 7,421,885 B2 * | 9/2008 | Kitzhoffer et al. | 73/38 |
| 7,458,251 B2 * | 12/2008 | Baklanov et al. | 73/38 |
| 7,568,379 B2 * | 8/2009 | Simon et al. | 73/38 |
| 2003/0094032 A1 * | 5/2003 | Baklanov et al. | 73/38 |
| 2011/0019207 A1 * | 1/2011 | Licitra et al. | 356/625 |

* cited by examiner

*Primary Examiner* — Tarifur Chowdhury
*Assistant Examiner* — Gordon J Stock, Jr.
(74) *Attorney, Agent, or Firm* — Luedeka, Neely & Graham, P.C.

(57) ABSTRACT

A method of measuring a porosity of a film, by measuring a refractive index of the film in a first environment having a first relative humidity to produce a first refractive index measurement. The refractive index of the film is measured in a second environment having a second relative humidity, where the first relative humidity is different from the second relative humidity, to produce a second refractive index measurement. Multiple gases can be used to create the first and second environments. The first refractive index measurement and the second refractive index measurement are input into a model that correlates refractive index to film porosity, to output the porosity of the film.

15 Claims, 2 Drawing Sheets

MEASUREMENT OF THIN FILM POROSITY

FIELD

This application claims all rights and benefits on U.S. provisional patent application 60/970,549 filed 2007 Sep. 7. This invention relates to the field of integrated circuits. More particularly, this invention relates to measuring properties of the materials used in the fabrication of integrated circuits.

BACKGROUND

The porosity of films used in the manufacture of integrated circuit devices has a tremendous impact on the performance of the devices. As the term is used herein, "integrated circuit" includes devices such as those formed on monolithic semiconducting substrates, such as those formed of group IV materials like silicon or germanium, or group III-V compounds like gallium arsenide, or mixtures of such materials. The term includes all types of devices formed, such as memory and logic, and all designs of such devices, such as MOS and bipolar. The term also comprehends applications such as flat panel displays, solar cells, and charge coupled devices.

The integrated circuit fabrication industry continues to develop porous films that are used as dielectric layers in the back end of the line of the circuit-making process. The dielectric constant of the films is reduced by increasing the amount of porosity, and this leads to faster switching times and improves device performance.

Consequently, there is a strong need to measure the porosity of films using fast, nondestructive techniques. In particular, the total porosity, pore size, and pore size distribution are parameters of interest for process monitoring and tool monitoring applications. Currently, most porosity measurements are performed using X-ray reflectivity or positron annihilation spectroscopy techniques, but these techniques are unsuitable for production environments.

What is needed, therefore, is a system that overcomes problems such as those described above, at least in part.

SUMMARY

The above and other needs are met by a method of measuring a porosity of a film, by measuring a refractive index of the film in a first environment having a first relative humidity to produce a first refractive index measurement. The refractive index of the film is measured in a second environment having a second relative humidity, where the first relative humidity is different from the second relative humidity, to produce a second refractive index measurement. The first refractive index measurement and the second refractive index measurement are input into a model that correlates refractive index to film porosity, to output the porosity of the film. The model can be one such as a computer program disposed on a computer readable medium, operable to instruct a computer to perform the calculations as described.

In this manner, the refractive index of a film, which is a relatively quick and easy measurement to take, can be used to determine the porosity of the film, which is a relatively long and difficult measurement to take. Thus, the porosity of the film can be more readily and cheaply determined in a production environment, which will enable integrated circuit fabricators to more closely monitor and control the porosity of the films that they use.

In various embodiments, the first environment and the second environment are created using gases having a plurality of different molecular sizes. In some embodiments the first relative humidity and the second relative humidity are both controlled to predetermined values. In some embodiments a first temperature of the first environment and a second temperature of the second environment are both controlled to predetermined values. In some embodiments the film achieves equilibrium in the first environment before measuring the first refractive index. In some embodiments the film achieves equilibrium in the second environment before measuring the second refractive index.

In some embodiments a plurality of measurements of the second refractive index are made, to determine a rate and a degree by which the second refractive index changes in the second environment. In some embodiments the rate by which the second refractive index changes in the second environment is used to determine a pore size distribution of the film, and the degree by which the second refractive index changes in the second environment is used to determine a total pore volume of the film.

The first environment is a relatively arid environment and the second environment is a relatively humid environment in some embodiments. In some embodiments the first environment is created with a first gas and the second environment is created with a different second gas. In some embodiments the first environment and the second environment are both created with a single gas, where the gas has a different moisture content in each environment. In some embodiments the first environment and the second environment are created using gases having a plurality of different molecular sizes.

According to another aspect of the invention there is described a method of correlating porosity to refractive index, by preparing a film sample, measuring the porosity of the film sample, measuring the refractive index of the film sample in a plurality of different environments, including at least different humidity, and establishing a correlation between the porosity of the film sample and the refractive index of the film sample in the different environments. In various embodiments of this aspect of the invention, the plurality of different environments additionally includes different temperature. In some embodiments the step of measuring the porosity of the film sample is accomplished by at least one of X-ray reflectivity or positron annihilation spectroscopy. In some embodiments the step of measuring the refractive index of the film sample is accomplished by at least one of ellipsometer and reflectometer.

According to yet another aspect of the invention there is described a model that correlates porosity properties for a film with refractive index properties for the film, where the refractive index properties for the film can be input to the model and the porosity properties for the film are output by the model. In various embodiments of this aspect of the invention, the model can be at least one of a mathematical module residing on a computer readable medium, a table of values of refractive index properties and porosity properties, and a plotted graph of values of refractive index properties versus values of porosity properties.

BRIEF DESCRIPTION OF THE DRAWINGS

Further advantages of the invention are apparent by reference to the detailed description when considered in conjunction with the figures, which are not to scale so as to more clearly show the details, wherein like reference numbers indicate like elements throughout the several views, and wherein.

DETAILED DESCRIPTION

This disclosure describes a new method to measure the porosity of thin films using optical techniques with high throughput on production substrates, and suitable for use in production environments.

The various embodiments of the invention combine the sensitivity of ellipsometry, reflectometry, or some other similar optical measurement method with the phenomenon of gas adsorption on porous films. Specifically, the embodiments of the invention observe the change in the measured refractive index of a film as it equilibrates between a humid environment and an arid environment. The measurements of refractive index can be taken continuously, discretely, or at "starting" and "ending" conditions. The change in the effective refractive index is then used as a correlated property to measure the porosity of the film being measured. The gases may consist of dry or moist inert or non-reactive gases. The change in effective refractive index can be measured at one or more wavelengths.

Figure 1:
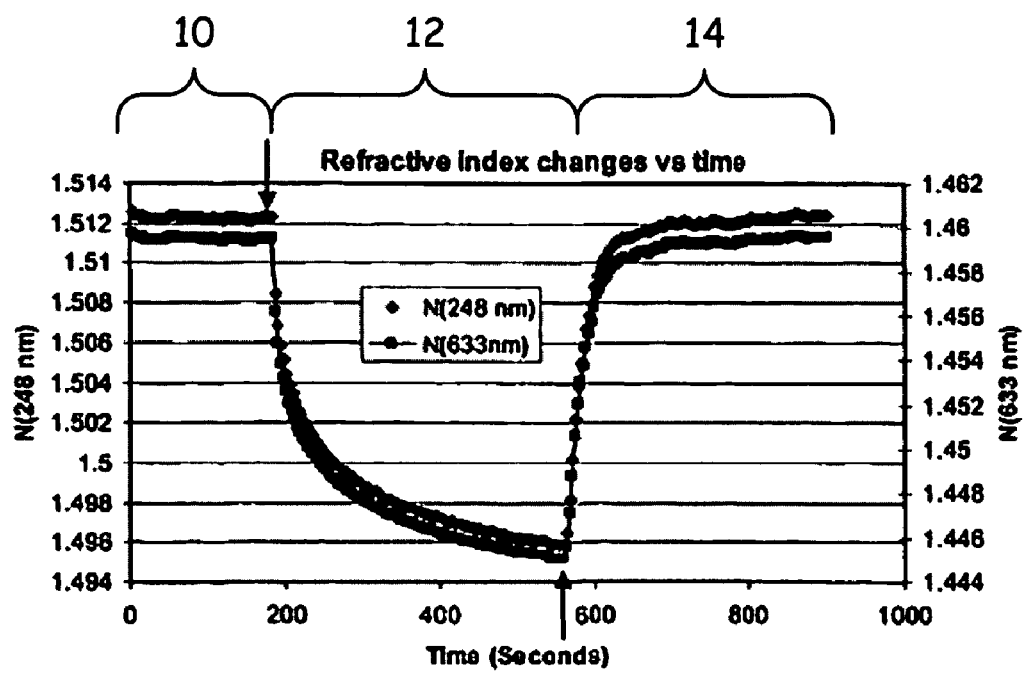
FIG. 1 is chart depicting the change in refractive index of a nominal five hundred angstrom porous oxide film that has been equilibrated to ambient air (about fifty percent relative humidity) when exposed to dry nitrogen.

FIG. 1 depicts the change in refractive index of a nominal five hundred angstrom porous oxide film when the film is exposed to dry nitrogen. In the initial phase 10, the substrate is exposed to ambient air, and the refractive index is observed to be essentially constant. During the second phase 12, dry nitrogen is allowed to flow over the measured area of the film, resulting in a rapid change in refractive index. The refractive index change exhibits a fast initial change followed by a period of slower change. The refractive index continues to decrease asymptotically until the nitrogen flow is stopped in phase 14. At this point there is a rapid recovery in the index of refraction, as the substrate is re-equilibrated with ambient air.

Figure 2:
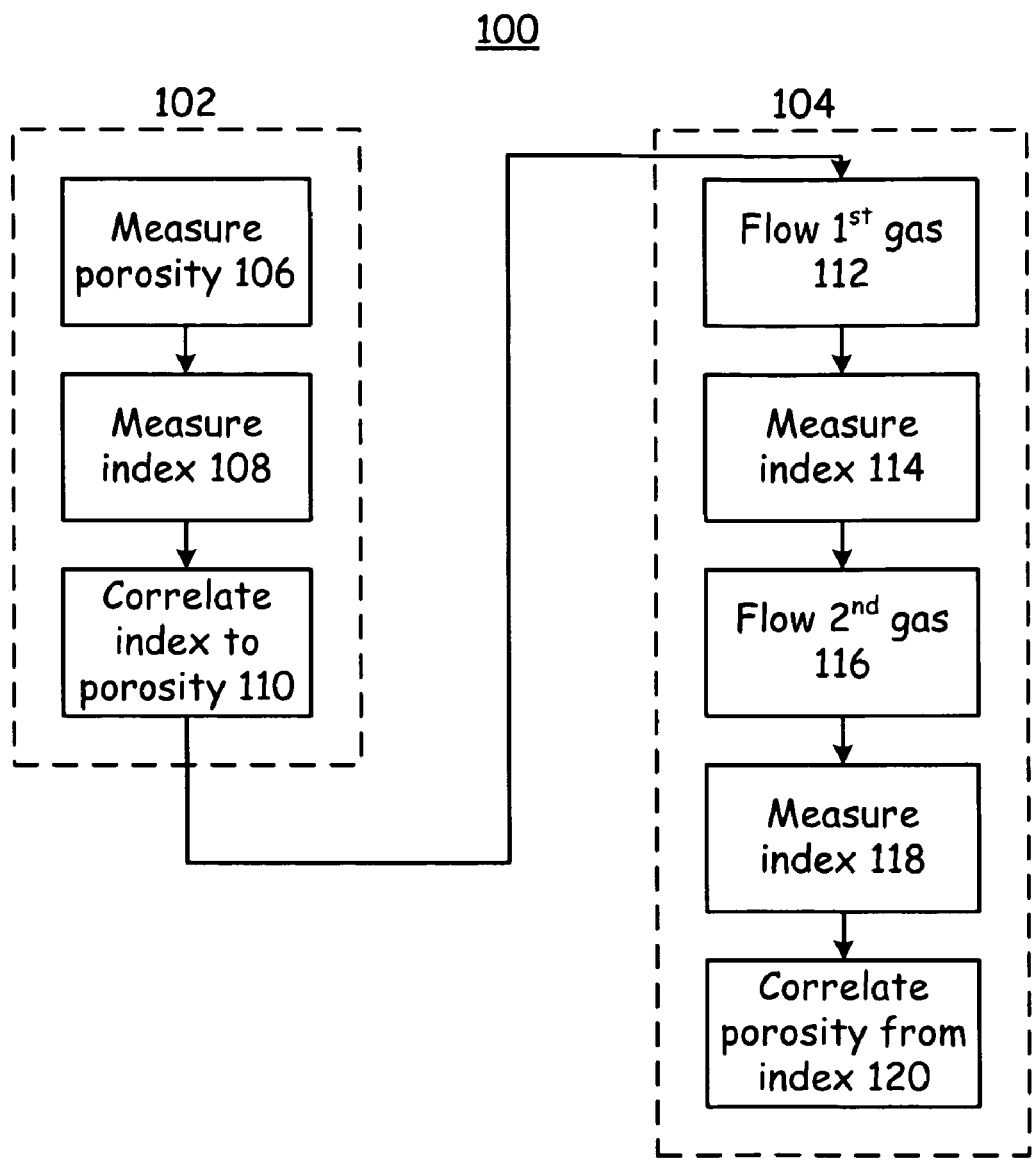
FIG. 2 is a flow chart of a method for determining the porosity of a film according to an embodiment of the present invention.

With reference now to FIG. 2, there is depicted a method 100 of determining porosity of a film according to an embodiment of the present invention. The method 100 according to the embodiment described has two portions 102 and 104. In this embodiment, the submethod 102 is an initial calibration procedure that would not have to be repeated every time. The submethod 104 is the measurement procedure that would be performed on every substrate on which a reading is desired.

The first step of the submethod 102, as given in block 106, is to measure the porosity of a film, using one of more tools suitable for such a purpose. This is preferably accomplished for a number of different films, and perhaps for a number of different films as formed by a number of different processes. In one embodiment, the porosity is measured of those films for which in-process measurements will be desired.

As given in block 108, the index of refraction is also measured for the films for which porosity was measured in block 106. This step can involve measuring the index of refraction with one or more tools suitable for such a purpose. This can be done for films that are measured in environments having different relative humidity properties, films at different temperatures—both the temperature of the film and the temperature of the environment, and films in environments that are created by different gases—such as gases with larger molecular sizes and gases with smaller molecular sizes. Preferably, the index of refraction is measured for these films under at least two environments for each temperature and pressure, where one environment is a relatively higher humidity environment, and the other environment is a relatively lower humidity environment. Measures of refractive index in these two environments are preferably made for all of the different gases, such as gases at different temperatures and gases of different molecular sizes.

The porosity measurements taken in step 106 are then correlated with the refractive index measurements, as given in block 100. The intent of step 110 is to produce a matrix of measurements that covers, at the very least, a range of parameters that would be indicative of a change of refractive index. However, some combinations of the parameters as exemplified above might induce a faster response in refractive index than other combinations, and thus might be more (or less) preferred than combinations of parameters that induce a slower response. In step 110, there is developed a chart or equation or some other means by which a refractive index measurement for a given film under a given set of conditions can be used to determine the porosity of that film. This correlation means is then used in the second submethod 104. Thus, this first submethod 102 might only need to be performed once to create the correlation between refractive index and porosity.

The submethod 104 is then performed regularly as desired, such as an in-process inspection of production substrates. In this submethod 104, a first gas having first properties is used to form the environment around the substrate, as given in block 112. With the environment of the first gas having been formed, and the substrate having come to equilibrium therein, an index of refraction is measured for the film, as given in block 116.

Once the substrate has equilibrated in the first environment and the index of refraction has been measured, the substrate is placed within an environment formed with a second gas, as given in block 116. It is appreciated that these environments can be formed in a number of different ways. For example, the first gas can be flowed into a chamber that holds the substrate, and then the second gas can be flowed in at a later point in time. Alternately, the substrate can be moved from one environment to another.

It is further appreciated that the first gas and the second gas might be the same gas, but with different moisture contents. For example, the first gas might be air having a relatively higher moisture content, and the second gas might be air having a relatively lower moisture content. Alternately, different gasses can be used for the first and second environments. In some embodiments the relatively humid environment is formed first and the relatively arid environment is formed second. In other embodiments the relatively arid environment is formed first and the relatively humid environment is formed second. In some embodiments the environment is changed between humid and arid more than once, while refractive index measurements are taken.

A measurement of refractive index is made for the substrate in the second environment, as given in block 118. This measurement can be a single measurement after the substrate equilibrates in the second environment, or is can be a series of measurements. In one embodiment the measurement comprises a series of measurements that are taken so quickly as to constitute a continuous reading of refractive index. By looking at the difference between the refractive index as measured in the first and second environments, the correlation as produced in the first submethod 102 can be used to determine the porosity of the film, as given in block 120. Thus, the embodiments of the present invention provide a quick and simple method of measuring porosity, such as on production substrates.

If the information gathered in the first submethod 102 supports it, then the information gathered in the second submethod 104 can yield even more information about the porosity of the film. For example based on modeling the rate at which the refractive index changes in the second environment and the magnitude of the change in refractive index, it is then possible to calculate the total pore volume (magnitude of the change) and the pore distribution (rate of change). Further, the use of gas molecules of different atomic sizes can yield information in regard to the pore size and the pore size distribution.

The foregoing description of preferred embodiments for this invention has been presented for purposes of illustration and description. It is not intended to be exhaustive or to limit the invention to the precise form disclosed. Obvious modifications or variations are possible in light of the above teachings. The embodiments are chosen and described in an effort to provide the best illustrations of the principles of the invention and its practical application, and to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. A method of measuring a porosity of a film, the method comprising the steps of:
    measuring a refractive index of the film in a first environment having a first relative humidity to produce a first refractive index measurement,
    measuring the refractive index of the film in a second environment having a second relative humidity, where the first relative humidity is different from the second relative humidity to produce a second refractive index measurement, and
    inputting the first refractive index measurement and the second refractive index measurement into a model that correlates refractive index to film porosity, to output the porosity of the film.

2. The method of claim 1, wherein the first environment and the second environment are created using gases having a plurality of different molecular sizes.

3. The method of claim 1, wherein the first relative humidity and the second relative humidity are both controlled to predetermined values.

4. The method of claim 1, wherein a first temperature of the first environment and a second temperature of the second environment are both controlled to predetermined values.

5. The method of claim 1, wherein the film achieves equilibrium in the first environment before measuring the first refractive index.

6. The method of claim 1, wherein the film achieves equilibrium in the second environment before measuring the second refractive index.

7. The method of claim 1, wherein a plurality of measurements of the second refractive index are made, to determine a rate and a degree by which the second refractive index changes in the second environment.

8. The method of claim 1, wherein a plurality of measurements of the second refractive index are made, to determine a rate and a degree by which the second refractive index changes in the second environment, and the rate by which the second refractive index changes in the second environment is used to determine a pore size distribution of the film, and the degree by which the second refractive index changes in the second environment is used to determine a total pore volume of the film.

9. The method of claim 1, wherein the first environment is a relatively arid environment and the second environment is a relatively humid environment.

10. The method of claim 1, wherein the first environment is created with a first gas and the second environment is created with a different second gas.

11. The method of claim 1, wherein the first environment and the second environment are both created with a single gas, where the gas has a different moisture content in each environment.

12. A method of correlating porosity to refractive index, the method comprising the steps of:
    preparing a film sample,
    measuring the porosity of the film sample,
    measuring the refractive index of the film sample in a plurality of different environments, including at least different humidity, and
    establishing a correlation between the porosity of the film sample and the refractive index of the film sample in the different environments.

13. The method of claim 12, wherein the plurality of different environments additionally comprises different temperature.

14. The method of claim 12, wherein the step of measuring the porosity of the film sample is accomplished by at least one of X-ray reflectivity or positron annihilation spectroscopy.

15. The method of claim 12, wherein the step of measuring the refractive index of the film sample is accomplished by at least one of ellipsometer and reflectometer.

* * * * *